United States Patent
Braig et al.

[11] Patent Number: 6,095,986
[45] Date of Patent: Aug. 1, 2000

[54] DISPOSABLE ANTI-FOG AIRWAY ADAPTER

[75] Inventors: James R. Braig, Piedmont; Daniel S. Goldberger, Boulder; Roger O. Herrera, Engeryville, all of Calif.; Mark L. Yelderman, Dallas, Tex.

[73] Assignee: Square One Technology, Inc., Boulder, Colo.

[21] Appl. No.: 09/123,232

[22] Filed: Jul. 28, 1998

[51] Int. Cl.⁷ ........................................................ A61B 5/08
[52] U.S. Cl. ...................... 600/532; D24/129; 128/204.23
[58] Field of Search ..................... 600/529–539; 128/897–898, 200.14–207.24; D24/129; D10/96; 250/343; 102/200.14–207.24

[56] References Cited

U.S. PATENT DOCUMENTS

| | | |
|---|---|---|
| 2,739,360 | 3/1956 | Voss . |
| 3,641,332 | 2/1972 | Redick et al. . |
| 3,727,050 | 4/1973 | Kerr . |
| 3,987,303 | 10/1976 | Stoft et al. . |
| 4,287,750 | 9/1981 | Eckstein et al. . |
| 4,467,073 | 8/1984 | Cressy . |
| 4,581,942 | 4/1986 | Ogura et al. . |
| 4,633,559 | 1/1987 | Loren . |
| 4,648,396 | 3/1987 | Raemer . |
| 4,662,369 | 5/1987 | O'Hara et al. . |
| 4,727,886 | 3/1988 | Conrardy et al. . |
| 4,772,790 | 9/1988 | Aldridge . |
| 4,810,924 | 3/1989 | Jelic . |
| 4,811,327 | 3/1989 | Petrov et al. . |
| 4,821,737 | 4/1989 | Nelson . |
| 4,823,457 | 4/1989 | Prochaska . |
| 4,914,720 | 4/1990 | Knodle et al. . |
| 4,944,294 | 7/1990 | Borek, Jr. . |
| 4,958,075 | 9/1990 | Mace et al. . |
| 4,998,018 | 3/1991 | Kurahashi et al. . |
| 5,018,957 | 5/1991 | Assink et al. . |
| 5,067,492 | 11/1991 | Yelderman et al. ..................... 600/532 |
| 5,081,998 | 1/1992 | Yelderman et al. . |
| 5,095,900 | 3/1992 | Fertig et al. . |
| 5,095,913 | 3/1992 | Yelderman et al. . |
| 5,237,984 | 8/1993 | Williams, III et al. . |
| 5,846,650 | 12/1998 | Ko et al. ................................. 428/336 |
| 5,957,127 | 9/1999 | Yamamori et al. ..................... 600/532 |

FOREIGN PATENT DOCUMENTS

| | | |
|---|---|---|
| 145 384 A2 | 6/1985 | European Pat. Off. . |
| 39 18 994 | 6/1990 | Germany . |
| WO 86 02820 | 5/1986 | WIPO . |

OTHER PUBLICATIONS

ATMER® 685, ICI Polymer Additives, Product Information Bulletin; *ICI Specialty Chemicals,* Wilmington, DE; 1990.

Solomon, "A Reliable, Accurate, $CO_2$ Analyzer for Medical Use," *Hewlett–Packard Journal,* pp.3–21, Sep. 1981.

*Primary Examiner*—Eric F. Winakur
*Assistant Examiner*—Michael Astorino
*Attorney, Agent, or Firm*—Woodcock Washburn Kurtz Mackiewicz & Norris LLP

[57] ABSTRACT

A disposable anti-fog airway adapter for use with a mainstream respiratory gas analyzer which provides a measurement of a patient's inhaled and exhaled gases. The airway adapter includes windows that are constructed of a thin, low heat capacity plastic that rapidly equilibrates to the temperature of the warm moist gases in the patient breathing circuit. In addition, the inside of the windows is also coated with an anti-fog surfactant either by laminating an anti-fog film with the window plastic prior to attaching the window to the airway adapter body or by first attaching the window to the airway adapter body and then applying the surfactant to the airway adapter after the window film is bonded in place so that the surfactant coats the entire inside of the adapter. The surfactant functions to increase the critical wetting tension of the surface it covers so that water on the window spreads into a uniform thin layer which does not absorb very much infrared energy and thus does not significantly reduce the signal strength. "Instant on" operation is accomplished because no heater and the like is necessary to warm up the windows to maintain them at an elevated temperature to prevent fogging. Numerous techniques are also provided for adhering the windows to the airway adapter body so that a substantially airtight seal may be obtained.

23 Claims, 8 Drawing Sheets

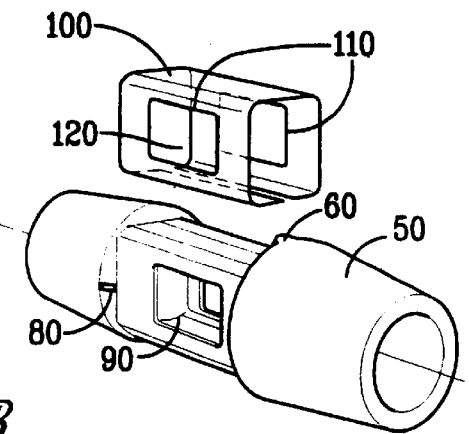
FIG. 3B
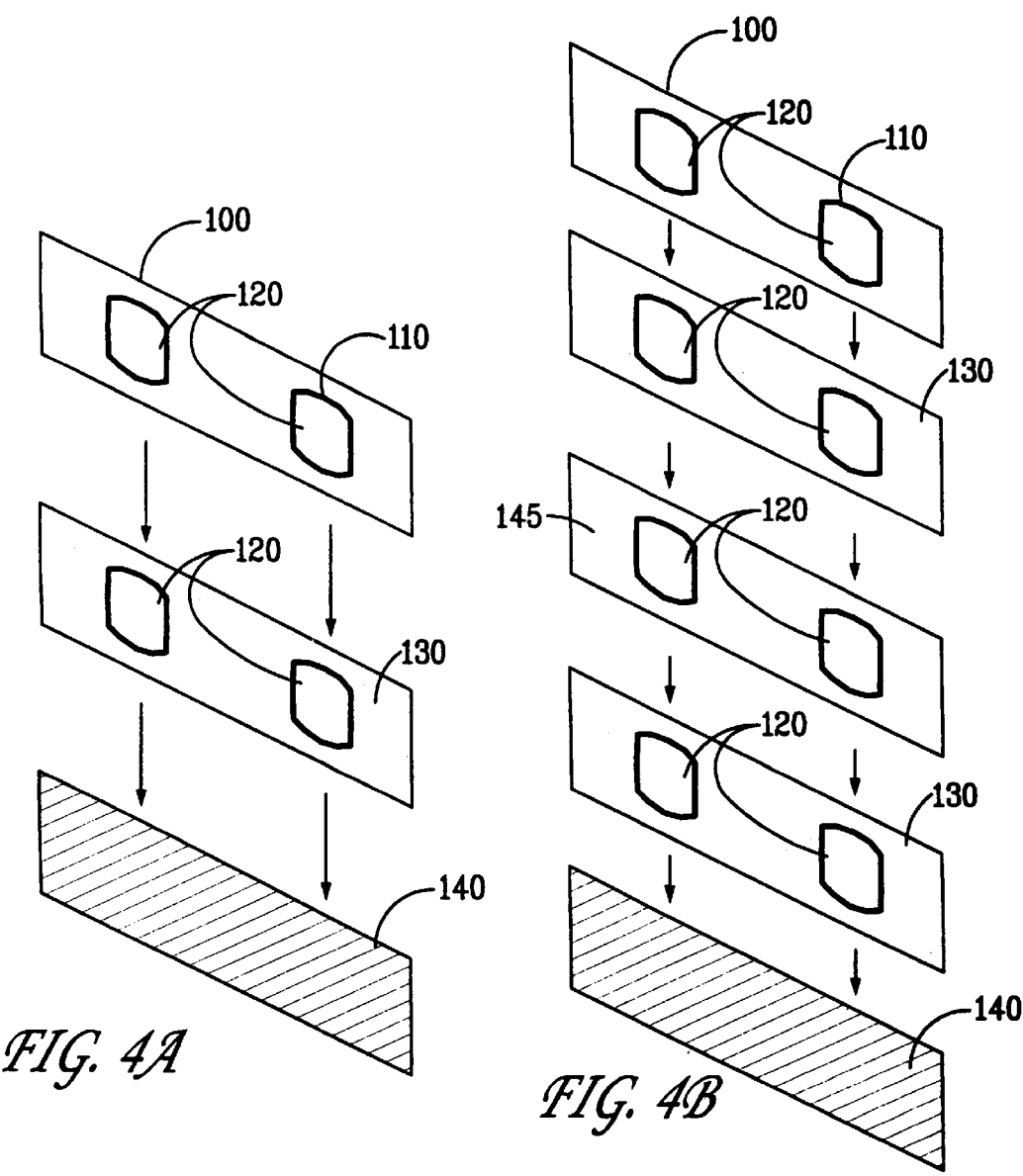
FIG. 4A
FIG. 4B

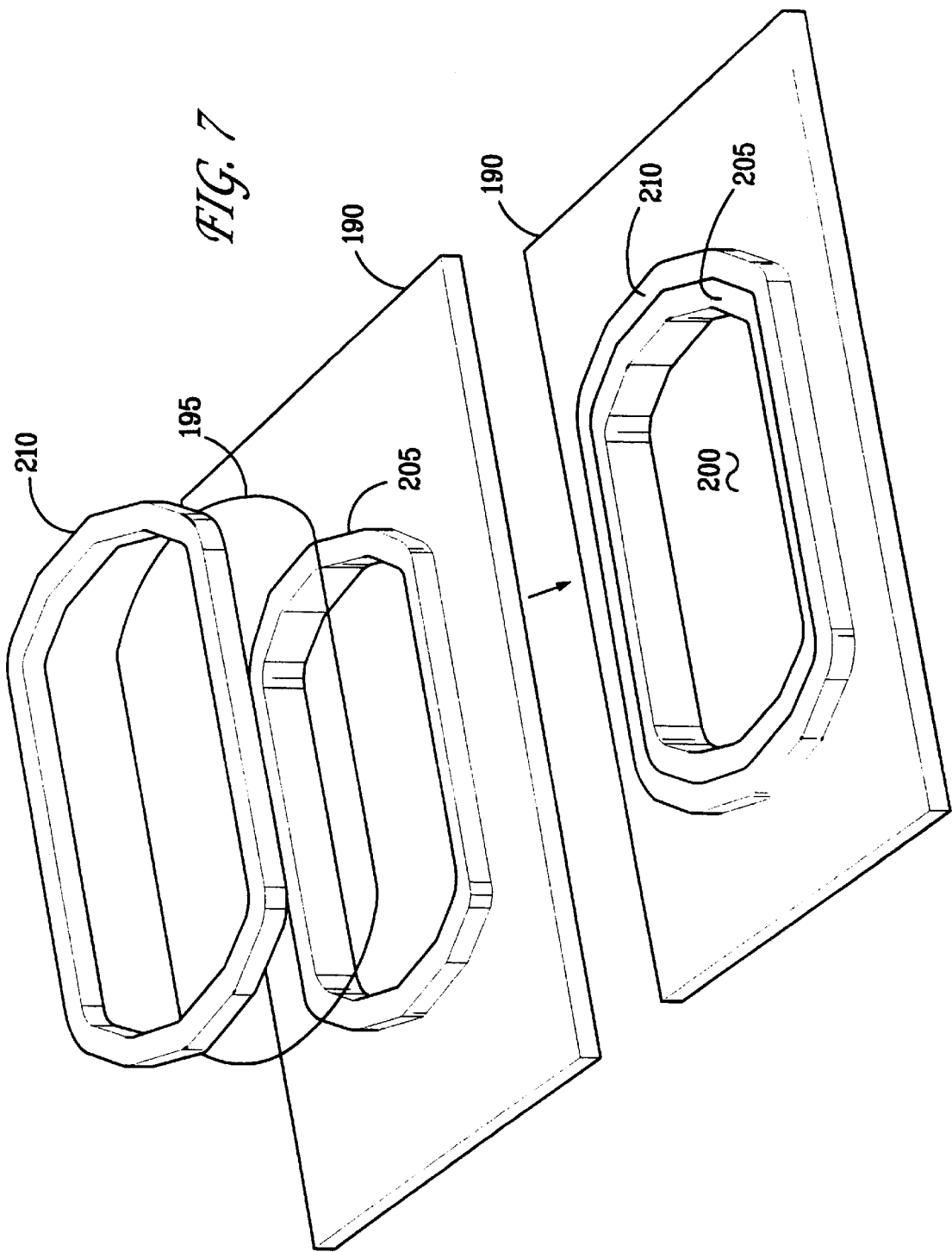

DISPOSABLE ANTI-FOG AIRWAY ADAPTER

CROSS-REFERENCE TO RELATED APPLICATIONS

The present application is a substitute application for abandoned U.S. patent application Ser. No. 07/984,673, filed Dec. 2, 1992, which is, in turn, a continuation-in-part application of abandoned U.S. patent application Ser. No. 756,455, filed Sept. 9, 1991, which is, in turn, a divisional application of U.S. patent application Ser. No. 564,179, filed Aug. 7, 1990, now U.S. Pat. No. 5,067,492.

BACKGROUND OF THE INVENTION

1. Field of the Invention

The present invention relates to a device which provides a conduit for patient respiratory gases and an optical channel for the passage of infrared radiation from a respiratory gas analyzer through the gases, and more particularly, to a disposable mainstream anti-fog airway adapter which has infrared transmissive windows treated by an anti-fog agent to prevent fogging by the patient's breath. The present invention also includes several techniques for forming the anti-fog windows and sealing them to the adapter body so that the adapter can be used with a mainstream respiratory gas analyzer.

2. Brief Description of the Prior Art

Mainstream respiratory gas analyzers provide a measurement of a patient's inhaled and exhaled gases by directing a beam of infrared energy across the patient's respiratory circuit and measuring the infrared absorption at the respective infrared frequencies. Mainstream respiratory gas analyzers are preferably located very close to the patient's mouth to provide accurate gas concentration measurements. Such measurements are very valuable at the time of intubation to determine if the endotracheal tube is properly located and during long term mechanical ventilation to determine the status of the patient's cardiopulmonary system. The patient's breathing circuit is a closed circuit, and the infrared energy enters and exits the respiratory gas stream by passing through "windows" which are typically located in the airway adapter. The "windows" are sections of a material that will pass the required wavelengths of infrared energy while maintaining an airtight seal of the patient's respiratory circuit.

Such infrared respiratory gas analyzers function by passing light of a specific wavelength (typically infrared) through a gas and measuring the amount of light that is absorbed. Such a respiratory gas analyzer is disclosed by Solomon in an article entitled "A Reliable, Accurate $CO_2$ Analyzer for Medical Use," *Hewlett-Packard Journal*, September 1981, pp. 3–21, for example. Solomon therein describes the HP $CO_2$ analyzer model 47210A Capnometer, which measures the amount of carbon dioxide in a patient's breath for medical diagnostic purposes. The HP model 47210A Capnometer is comprised of an airway adapter, a sensor and a processor box. The airway adapter described by Solomon is a hollow aluminum casting with sapphire windows which is inserted in series with the ventilator plumbing and is used to keep the patient's respiratory gases from coming into contact with the sensor mechanism. The sensor is snapped over the airway adapter windows, and the measurement is made directly on the airway through which the patient is breathing. The sensor contains all the optical components necessary to make the infrared measurement and is connected to the processor box by a cable. The processor box powers the sensor, processes the return signal, and presents the data via an LED display.

The airway adapter of the HP model 47210A Capnometer is made of aluminum so that it can be sterilized and adapted to meet a number of other critical requirements such as small size, light weight, stable infrared path length, ruggedness and uniformity. It has become desirable to develop an airway adapter which is disposable and hence useful for preventing infection through cross-contamination. However, such a disposable airway adapter must still meet numerous critical requirements, such as those just enumerated, in order to provide sufficient accuracy of measurement.

A respiratory gas analyzer utilizing an interchangeable, low cost disposable airway adapter suitable for single patient use is described in U.S. Pat. Nos. 5,081,998 and 5,095,913, while an embodiment of a disposable airway adapter for such a system is described in U.S. Pat. No. 5,067,492, all of which are assigned to the same assignee as the present invention. As described in those patents, the airway adapter must provide a sealed, tubular passage for the unobstructed flow of respiratory gases while also providing an optical path through the respiratory gases which are in the portion of the airway adapter between the windows. The windows must be transparent to the infrared wavelengths used to analyze the constituent gases, and the optical path length defined by the airway adapter and infrared absorption fingerprint of the infrared windows must remain constant among interchangeable adapters for accuracy of measurement. Also, in order for the airway adapter to be disposable, means must be provided for accurately locating the airway adapter in the respiratory gas analyzer such that the optical path length through the respiratory airstream remains a constant length. For example, as described in U.S. Pat. No. 5,067,492, the airway adapter may snap fit into the respiratory gas analyzer.

The airway adapter described in U.S. Pat. No. 5,067,492 is comprised of a tubular body and thin plastic windows. The adapter body is preferably injection molded out of polycarbonate or styrene acrylonitrate (SAN). The plastic windows, on the other hand, are preferably fabricated from a polyester film (such as DuPont. Mylar® 100 XM963) with a thickness of 0.001 inch +/−0.0005 inch. The polyester film windows are then sealed to the adapter body so that there are no gas leaks and so that the film is maintained in tension. This tensile "prestressing" prevents wrinkles from developing under reasonable temperature excursions and prevents the windows from bulging during reasonable pressure excursions within the respiratory gas circuit, for the calibration of the gas analyzer system could be adversely affected if the windows were allowed to bulge more than the allowable tolerance of the optical path length.

However, a problem has been encountered with "mainstream" respiratory gas detectors of the type described in the aforementioned patents. Namely, for enhanced patient care for long-term ventilated patients, the inspired gases are often heated to body temperature and humidified. In addition, even in short cases where humidification is not required, the patient's exhaled gas is almost fully saturated with water vapor at body temperature. This water vapor has been found to condense on the airway adapter and on the infrared windows, thereby posing an obstacle to the transmission of the infrared energy through the windows. The condensed water is troublesome to measurements because it absorbs infrared energy, thereby reducing the signal strength. In addition, the water often condenses in droplets which act as small lenses which distort the infrared energy and further increase the attenuation of the infrared signal due to the physical thickness of the droplets. The present inventors have set out to solve this problem.

Traditional solutions to the condensation problem involve heating the windows to a temperature above body temperature to prevent condensation. This solution is effective but has several inherent problems. For example, the heat takes time to develop after the instrument is turned on. This makes "instant on" operation of the analyzer impossible. Since one of the uses of the analyzer is verification of proper intubation, the ability to simply turn the instrument on and use it without "warm-up" is valuable, and having to wait for "warm-up" may render the instrument useless in a critical intubation procedure. In addition, generation of the heat requires power. Since some monitors are used in a "transport" mode where the monitoring equipment is powered by internal batteries, the use of additional power to heat the windows is a disadvantage. This requires the batteries to be larger and heavier and/or the useful life of the instrument operating on the battery to be reduced. Moreover, the heat can be dangerous to the patient. Heating the windows to above body temperature could cause patient burns if the heated analyzer came into contact with the patient's skin. Furthermore, the warm, dry nature of the infrared window maintained at an elevated temperature promotes the adhesion of other patient secretions such as blood and mucus if they are coughed up into the airway. These contaminants can block the :infrared energy and render the analyzer inoperative.

Accordingly, the present invention is designed to solve the aforementioned problems caused by water condensation and the like on the windows of a disposable airway adapter. The present inventors know of no other suitable prior art disposable airway adapter and hence believe that no one has previously recognized the problem which is to be solved by the present invention. Thus, the present inventors also know of no prior art technique besides that described above for preventing the condensation of water droplets from a patient on the windows of a mainstream airway adapter. The present invention is thus believed to be the first attempt to meet such needs.

SUMMARY OF THE INVENTION

The present invention provides an inexpensive disposable anti-fog airway adapter which overcomes the above-mentioned problems caused by the condensation of water and the like on the windows of a mainstream airway adapter. The present invention provides techniques for treating the plastic film windows and the surface inside the airway adapter with an anti-fog coating which enhances the ability of the windows to resist fogging caused by condensing moisture and allows the windows to shed any liquid which might otherwise obstruct the optical path. For example, the anti-fog coating can be applied by spraying or washing the interior surfaces of the finished airway adapter with a suitable non-toxic surfactant such as Atmer™ 685 manufactured by ICI Specialty Chemicals. On the other hand, the windows may be formed of polymer films which are laminated with such an anti-fog impregnated coating and then adhered to the body of the airway adapter to provide an airtight seal. The present invention thus solves the aforementioned problems due to water condensation without adversely affecting the low cost and disposable nature of the airway adapter.

A preferred embodiment of the present invention thus relates to an endotracheal airway adapter for use in a respiratory airstream of a patient in proximity of the patient's mouth during quantitative measurement of the concentration of respiratory constituents of the patient using a mainstream respiratory gas analyzer having infrared transmission and detection devices disposed in a housing which receives the airway adapter. Such an airway adapter in accordance with a preferred embodiment of the invention comprises a substantially tubular portion having a pair of thin plastic windows which are disposed between the infrared transmission and detection devices during gas measurement. Preferably, the substantially tubular portion is comprised of a material which is slightly deformable and has oppositely disposed openings in a width-wise direction thereof which lie in an optical path between the infrared transmission and detection devices when received by the housing. The pair of thin plastic windows, on the other hand, are preferably disposed over the respective oppositely disposed openings of the tubular portion and adhered thereto so as to form a substantially airtight seal and so as to be a predetermined distance from each other during the quantitative measurement of the concentration of respiratory constituents of the patient using the infrared transmission and detection devices. However, the airway adapter of the invention is particularly characterized in that the windows which pass the infrared energy from the infrared transmission device to the detection device are treated with a non-toxic surfactant so as to prevent fogging of the windows when they are placed in the respiratory airstream of the patient in the vicinity of the patient's mouth.

In a preferred embodiment, the tubular portion of the airway adapter is preferably injection molded out of polycarbonate or styrene acrylonitrate (SAN) or formed of aluminum, while the windows are preferably formed in a single thin plastic layer comprising at least one of polyester, polypropylene and polyethylene. The window preferably includes an impregnated anti-fog surfactant so as to form an anti-fog film which is approximately 1 to 1.5 mil thick. Such an anti-fog film is then wrapped about the tubular portion such that the windows are disposed over the respective oppositely disposed openings before being sealed to the tubular portion using an adhesive. Preferably, the adhesive is selectively applied so that no adhesive appears in the "optical path" of the window. The adhesive is preferably a heat seal adhesive whereby the substantially airtight seal is formed by heat sealing the anti-fog film to the tubular portion during wrapping, or the adhesive may be a pressure sensitive adhesive whereby the substantially airtight seal is formed by applying pressure between the anti-fog film and the tubular portion during wrapping.

In addition, in order to improve heat distribution, a thin copper layer may be placed between the anti-fog film and the tubular portion during wrapping so that no portion of the copper appears in the "optical path" of the windows. This copper layer provides improved heat distribution from the source side to the detector side of the adapter so that condensation on the detector side is minimized and optimal use is made of the source heat. To further decrease the adverse effects of water droplets on the infrared measurement, the inside portion of the adapter adjacent the window preferably is designed to include "gutters" for channeling condensed water droplets away from the sills formed at the window openings.

In an alternative embodiment, the windows of the airway adapter may be treated with the non-toxic surfactant by pouring a solution containing the non-toxic surfactant into the airway adapter so as to flow over the windows, draining the solution and then drying the windows in warm air. Since the anti-fog film is not integral with the window, the windows may be made in any of a number of ways before being coated with the non-toxic surfactant.

For example, as in the above-mentioned embodiment, the windows may be formed in a single thin plastic layer which is wrapped about the tubular portion such that the windows are disposed over the respective oppositely disposed openings before being sealed to the tubular portion using an adhesive.

On the other hand, in another embodiment the windows maybe formed by stretching a sheet of polymer film treated with a thin layer of heat seal adhesive to a predetermined tension, heat sealing respective window frames to the stretched polymer film so as to form respective window assemblies, and then sealing the respective window assemblies into the respective oppositely disposed openings by at least one of solvent bonding and ultrasonic welding.

In yet another embodiment, the windows may be adhered to the tubular portion by heat staking or snap-fitting a drum band disposed over the windows around the periphery of the oppositely disposed openings.

In still another embodiment, the tubular portion and the windows may be injection molded from the same shot of plastic and the thin windows formed by hot stamping the portion of the plastic in the respective oppositely disposed openings. The hot stamped windows may then be polished to optical quality.

In yet another embodiment, the windows may be formed by extruding a polymer film into a tube, disposing the tube about the tubular portion such that the tube is located over the respective oppositely disposed openings, and then heat shrinking the tube until the tube and the tubular portion form the substantially airtight seal.

The scope of the invention also includes a method of making a disposable endotracheal airway adapter of the type described above, comprising the steps of:

molding from a material which is slightly deformable a substantially tubular portion for placement in the respiratory airstream of the patient, the tubular portion having oppositely disposed openings in a width-wise direction thereof which lie in an optical path including a portion of the respiratory airstream of the patient which is between the infrared transmission and detection devices when the tubular portion is received by the housing;

forming a pair of plastic windows from a thin layer of plastic;

disposing the windows over the oppositely disposed openings of the tubular portion so that the windows are a predetermined distance from each other during the quantitative measurement of the concentration of respiratory constituents of the patient using the infrared transmission and detection devices and so that the windows pass infrared energy from the infrared transmission device to the detection device through the respiratory airstream of the patient;

adhering the windows to the tubular portion so as to form a substantially airtight seal; and treating the pair of windows with a non-toxic surfactant so as to prevent fogging of the windows when the windows are placed in the respiratory airstream of the patient.

Of course, the windows may be permanently treated with the non-toxic surfactant by forming the thin window layer from a material including an integral surfactant, or the windows may be temporarily treated with the anti-fog coating by pouring a solution of the non-toxic surfactant into the airway adapter so as to flow over the windows and drying the windows before use. Such windows may be formed in accordance with any of the window forming techniques described above.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings, of which:

FIGS. 3(a)–(b) together illustrate a first preferred embodiment of an anti-fog airway adapter manufactured in accordance with the techniques of the invention.

FIG. 4(a) illustrates an expanded view of the anti-fog film, the transfer adhesive layer and the release liner of the windows of the airway adapter of the embodiment of FIG. 3.

FIG. 4(b) illustrates an expanded view of an anti-fog film as in FIG. 4(a) which has been modified to further include a copper layer for improving heat distribution.

FIG. 7 illustrates an exploded closeup view of the drum head assembly of an anti-fog airway adapter in accordance with the embodiment of FIGS. 6(a)–(c).

DETAILED DESCRIPTION OF THE PRESENTLY PREFERRED EMBODIMENTS

A disposable anti-fog airway adapter in accordance with presently preferred exemplary embodiments of the invention will be described below with reference to FIGS. 1–8. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

Figure 1:
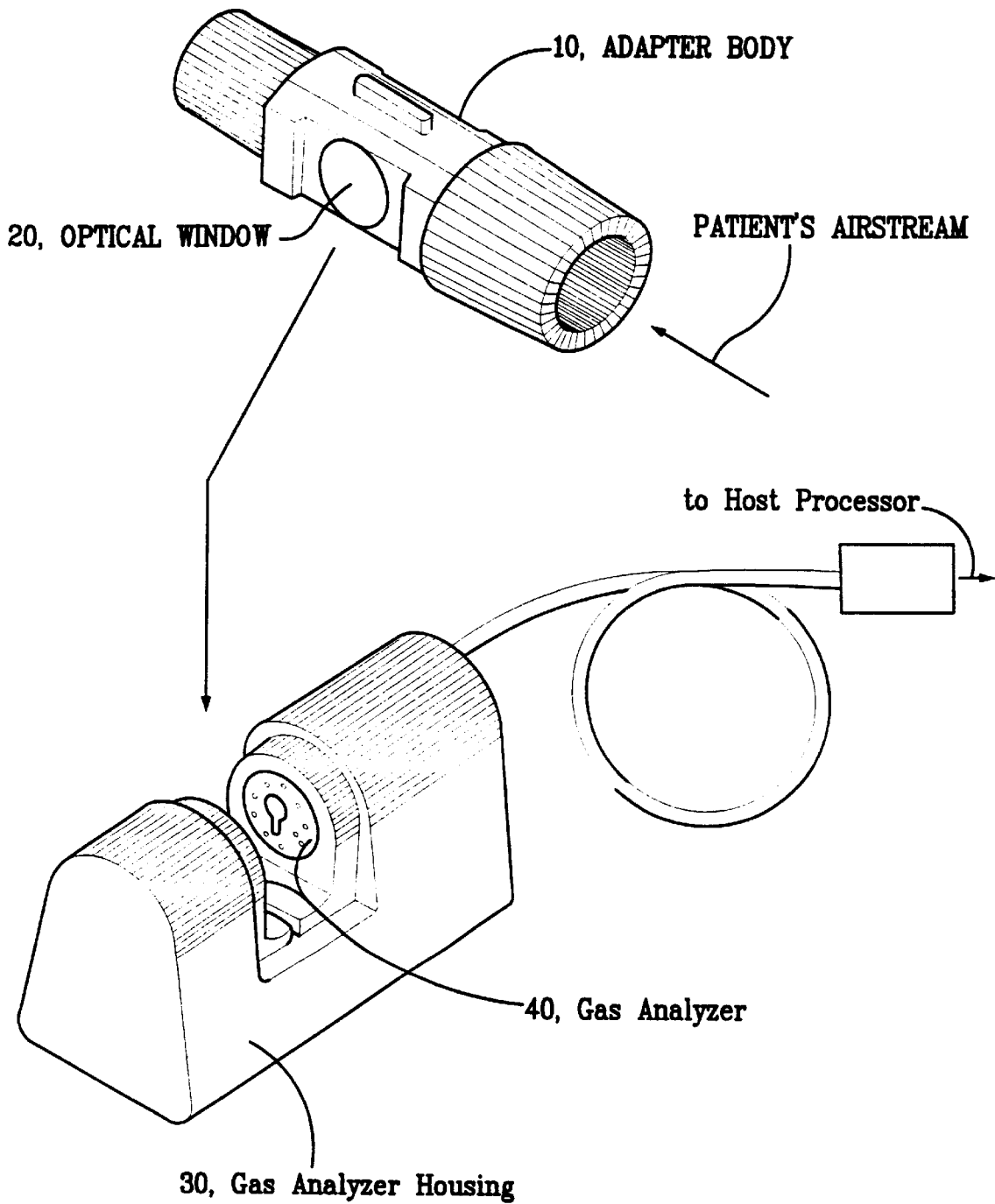
FIG. 1 illustrates a perspective view of a mainstream infrared gas analyzer and a disposable airway adapter of the type described in the aforementioned parent applications.
Figure 2A:
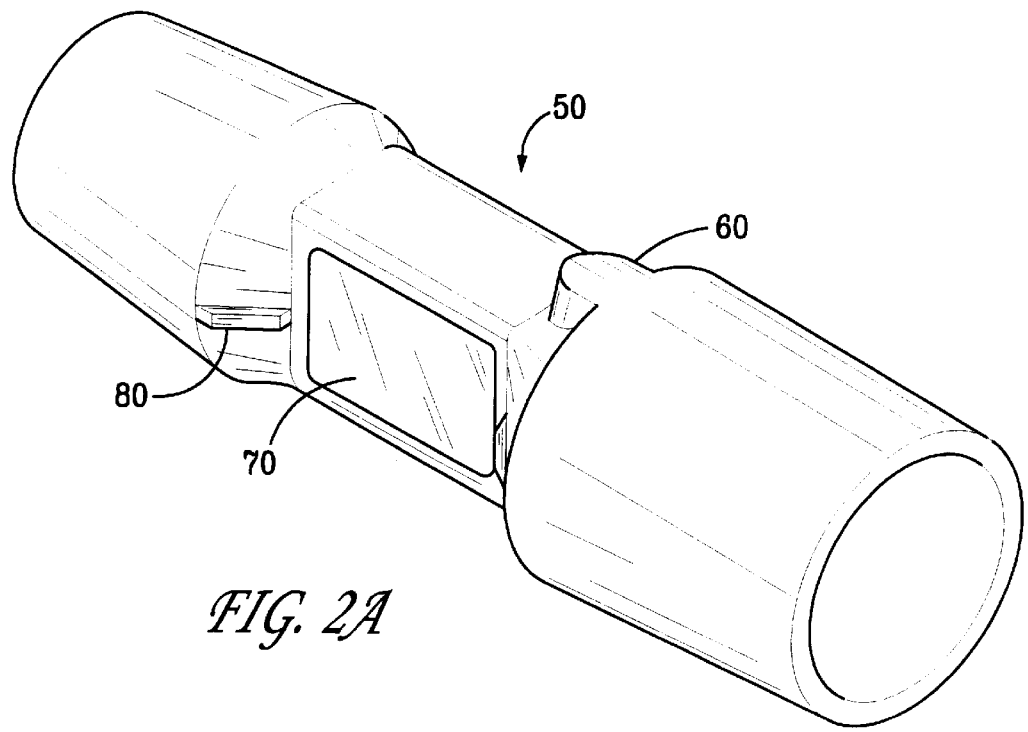
FIG. 2(a) is a top right perspective view of an airway adapter according to an embodiment of the invention.
Figure 2B:
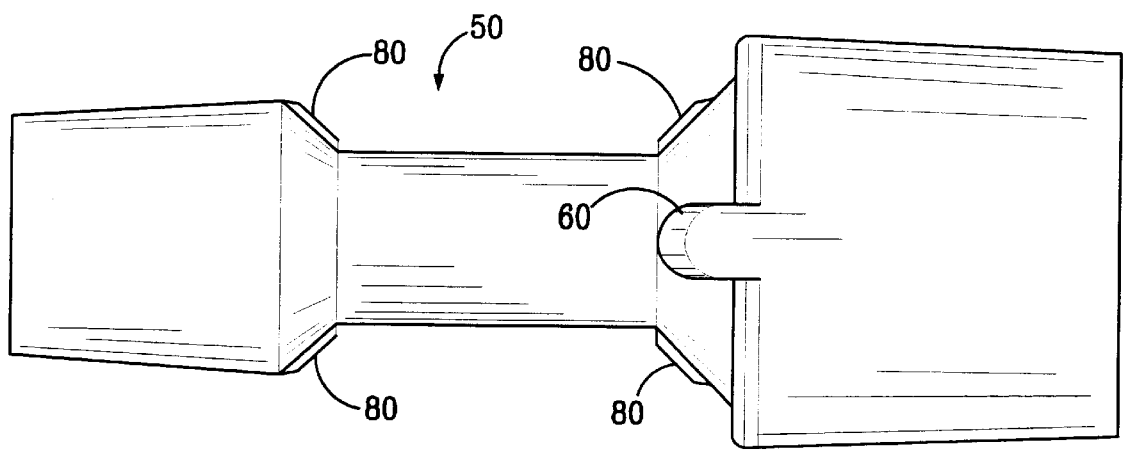
FIG. 2(b) is a top plan view of the airway adapter of FIG. 2(a).
Figure 2C:
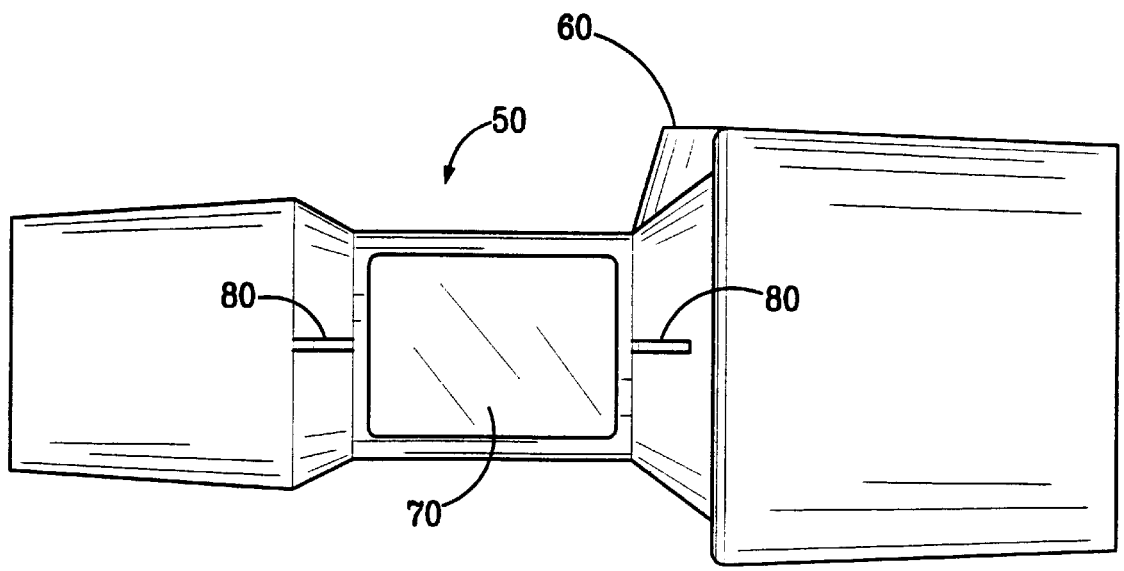
FIG. 2(c) is a front elevational view of the airway adapter of FIG. 2(a).
Figure 2D:
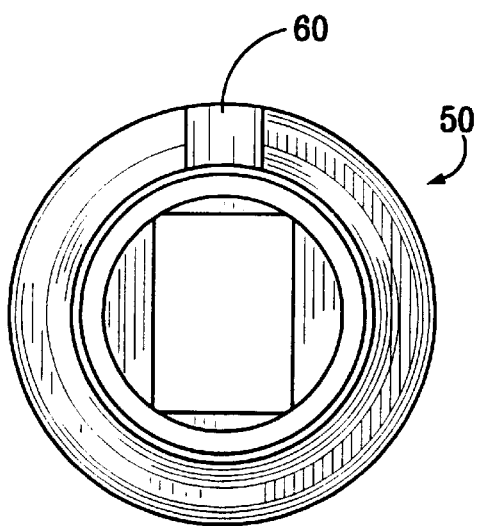
FIG. 2(d) is a left end elevational view of the airway adapter of FIG. 2(a).
Figure 2E:
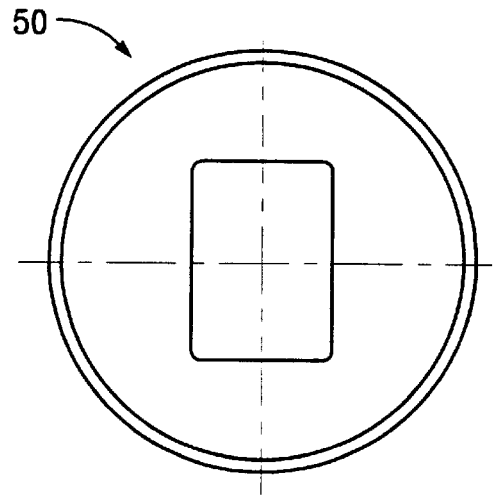
FIG. 2(e) is a right end elevational view of the airway adapter of FIG. 2(a).

A mainstream respiratory gas analyzer and disposable airway adapter of the type described in the aforementioned parent applications is illustrated by way of example in FIG. 1. As shown, the airway adapter body 10 is disposed directly in the patient's airstream so as to receive respiratory gases from the patient. Optical windows 20 of the airway adapter are formed on respective sides of the adapter body 10 so that when the airway adapter body 10 is placed within the gas analyzer housing 30 the optical windows 20 are disposed in the optical path of the gas analyzer 40. Then, as described in the aforementioned parent applications, the detected absorption signals from the gas analyzer 40 are output to a host processor for calculation of the concentration of the respiratory gases.

The present invention relates to an improved disposable airway adapter for use in such a system. As with the airway adapter of U.S. Pat. No. 5,067,492, the present invention relates to a disposable airway adapter which is used to keep the patient gases being monitored from coming into contact with the respiratory gas analyzer mechanism. The body of the airway adapter of the invention is designed to connect in series with the airway tubing used to connect the patient to a mechanical respirator or anesthesia breathing circuit. The disposable airway adapter body is preferably very light in weight so that it does not interfere with the breathing tube which is usually inserted into the patient's trachea. In addition to being a gas conduit, the airway adapter of the invention also provides an optical window through which the gas analyzer can pass light onto the sample for analysis.

One key property of the optical windows used in the disposable airway adapter of the invention is that they are low in cost. They are ideally made of the same material and molded as part of the body of the adapter using any of the manufacturing processes described below. The low cost windows and low cost body of this device allow it to be disposed of after use on a single patient so as to save sterilization expenses and to eliminate cross-contamination. This is especially useful with highly contagious diseases such as Tuberculosis, but is also a benefit in routine cases were unknown diseases may be carried but not active. Also, since the airway adapter of the invention is relatively small and light in weight, it may be placed close to the patient's mouth so as to allow quantitative readings for purposes of determining the concentrations of the constituents in the expired air.

The disposable airway adapter in accordance with the invention is designed for use with the gas analyzer housing 30 illustrated in FIG. 1 and hence is preferably designed to snap-fit into the housing 30 of the gas analyzer 40, which is preferably of the type described by the present inventors in the aforementioned related patents, the contents of which are hereby incorporated by reference in their entirety as if set forth fully herein. As shown, portions of the gas analyzer 40 are designed to protrude and slightly "squeeze" the optical windows 20 of the adapter 10 so as to accurately locate the optical windows 20 in place in front of the detectors of the gas analyzer 40 so that the membranes of the optical windows 20 are a predetermined distance from each other. As described in the aforementioned parent application, this "optical path length", L, is maintained precisely by the rigid housing of the gas analyzer 40 without requiring precision and strength of the airway adapter 10. The present invention is thus characterized in that the optical path length is maintained by the durable gas analyzer 40, not the disposable airway adapter 10 per se.

FIGS. 2(a)–(e) illustrate respective views of an embodiment of an anti-fog airway adapter 50 in accordance with the invention. The airway adapter illustrated in FIGS. 2(a)–(e) is preferably formed of a polycarbonate or styrene acrylonitrate using plastic injection molding techniques. For this purpose, a plastic injection "gate" 60 is provided for injection molding the airway adapter 50. The material and the shapes used in forming the airway adapter 50 of the invention render it slightly deformable such that when the adapter is placed in contact with the gas analyzer 40 the adapter assumes or conforms to the shape of the gas analyzer 40, particularly the window to window spacing. The spacing between entry and exit windows 70 is critical to the proper operation of the gas analyzer 40 and is controlled by the gas analyzer 40 by pressing the pliable adapter body 50 into shape when the adapter is installed into the gas analyzer housing 30 as illustrated in FIG. 1. In other words, the airway adapter 50 in accordance with the invention is designed such that it conforms to the gas analyzer housing 30 of the gas analyzer 40 so that its precision "optical path length" may be maintained even when a less expensive material such as plastic or aluminum is used to form the airway adapter 50. For this purpose, tabs 80 are used to snap fit the airway adapter 50 into the gas analyzer housing 30. This leads to the disposable nature of the invention.

As shown in FIGS. 2(a)–(e), the airway adapter 50 has respective tapered ends for connecting the airway adapter 50 to respective airway tubes from the patient. The connecting portions are sufficiently tapered so as to conform to standard conical fittings of the type set forth by the American National Standard (ANSI Standard) Z79.6-1975. As shown, the airway adapter 50 also includes windows 70 which are spaced at the optimum "optical path length" distance, L, from each other. As noted above, prior art windows have had problems with fogging. Hence, anti-fog optical windows 70 in accordance with the invention have been designed which now will be described with respect to FIGS. 3–7.

As noted above, moisture condensation on infrared windows has been a problem in prior art airway adapters. The resulting fog absorbs some portion of the infrared energy and adversely affects the analyzer measurements. The fog is created when warm, moist gases inside the respiratory circuit react with cooler optical windows of the airway adapter. Prior art devices have addressed this problem by using sapphire as the window material, which has a relatively high mass and high heat capacity. However, fogging problems are reintroduced when thin plastic windows are used in place of the sapphire windows of the prior art.

As used herein, the term "fog" describes the condensation of water vapor on the surface of a transparent plastic film in the form of small discrete droplets. The physical conditions that lead to this phenomenon include: the temperature of the inside surface of the film falls below the dew-point of the enclosed air/water vapor mixture; the air near the film cools to a temperature at which it can no longer retain all of the water vapor so that excess water condenses upon the film; and the existence of a difference between the surface tension of the condensed water and the critical wetting tension of the film surface which causes the water to condense as discrete droplets rather than as a continuous film.

The present inventors have discovered that water vapor condenses on the windows of an airway adapter so as to adversely affect the transmission of the infrared energy through the windows. The present inventors have solved this problem by forming the windows of a thin, low heat capacity plastic, such as polyester, polypropylene or polyethylene, of a thickness on the order of 0.001 inch. In a preferred embodiment of the invention, for example, a polyester film which is 0.001 inch thick is chosen for its strength and infrared transmission characteristics. Such a thin film provides a window that rapidly equilibrates to the temperature of the warm, moist gases in the patient's breathing circuit. Since the windows rapidly equilibrate at the temperature of the airway gases, condensation is minimized. "Instant On" operation is thus accomplished because no heater is necessary to maintain the windows at an elevated temperature.

The anti-fog windows of the airway adapter of the invention are further characterized in that the inside of the window is further coated with an anti-fog surfactant. To the present inventors' knowledge, anti-fog surfactants have not been used in the context of mainstream airway adapters. The present inventors are thus the first to discover that fogging of the windows of the airway adapter windows may be minimized by apply a non-toxic surfactant to the windows of a mainstream airway adapter. While several such surfactants have been used in the area of agricultural films and food packaging films, the present inventors are believed to be the first to adapt such films for use in airway adapters of the type described in the aforementioned parent application. For example, a preferred embodiment of the invention uses Atmer® 685 manufactured by ICI Specialty Chemicals in Wilmington, Del. as a surfactant. This surfactant is preferably mixed in a solution containing 7% ethanol, 5% Atmer® 685 and 88% water and is then placed inside the airway adapter 50, drained, and then dried in warm (150° F.) air for 15 minutes. Preferably, the surfactant is applied to the airway adapter 50 after the window film is bonded in place so that the surfactant coats the entire inside of the airway adapter 50. Also, as will be described with respect to FIG. 3, the surfactant can also be incorporated into the plastic of the airway adapter 50 and window film 70 at the time of molding. Alternative embodiments including an impregnated surfactant will be described below with reference to FIGS. 4–7.

The surfactant acts to increase the "critical wetting tension" of the surface it covers. The result is a reduction in contact angle between the water and plastic surface, thereby permitting the water to spread into a uniform thin layer. This thin layer does not absorb very much infrared energy and does not significantly reduce the signal strength. The thin layer of water also provides a "self cleaning" window surface. Hence, when patient secretions are "coughed up" into the airway, they do not stick to the windows. After the secretions have drained away, any secretions that came in contact with the thin layer of water covering the window are also drained away. The secretions are thus not able to adhere to the window because of the thin layer of water protecting the surface.

Atmer® 685 is a presently preferred non-toxic surfactant which uses an internal. anti-fog additive in its polymer formulation to provide surface active or wetting agents which are designed to have a controlled incompatibility with the polymer matrix. When a film is formed from a solution of Atmer®, these additives are uniformly dispersed throughout the thickness of the film but subsequently migrate to the film surface where they increase the critical wetting tension. The result is a reduction in contact angle between the water and the polymer surface, which, as noted above, permits the water to spread into a more uniform layer. The resulting transparency removes the optical barrier caused by the discrete droplets and overcomes the undesirable effects described above. Adoption of an internal additive distributed throughout the solution thus leads to a "reservoir" effect which increases the useful life of the anti-fog agent.

Atmer® 685 is also desirable since it does not cause any known physical or health hazards and has been approved by the FDA for the packing of food. Hence, Atmer® 685 is safe for use in a closed respiratory circuit. However, it is important to avoid using excessive amounts of anti-fog additives in the polymer films since the surface blooming that may occur will reduce both printability and sealability of the film. Other FDA approved non-toxic films besides Atmer® 685 which may used in accordance with the invention include Atmer® 645, which is also available form ICI Specialty Chemicals, Exxene® M-1 available from Exxene Corporation, and Pluronic® F-68 available from BASF Corporation.

Each of the embodiments of the invention comprises a molded plastic airway adapter body and infrared transmissive plastic film windows. However, if desired, the airway adapter body may be formed of aluminum. The specially treated film from which the windows are formed in accordance with the invention provides a non-fogging window for continuous use of the airway adapter in a highly humidified breathing circuit with virtually no maintenance required. Unlike other systems that require heat and time to prevent fogging of the windows, the airway adapter of the invention enables the gas analyzer to provide accurate and consistent gas readings even under highly humidified airways immediately after power on.

Figure 3A:
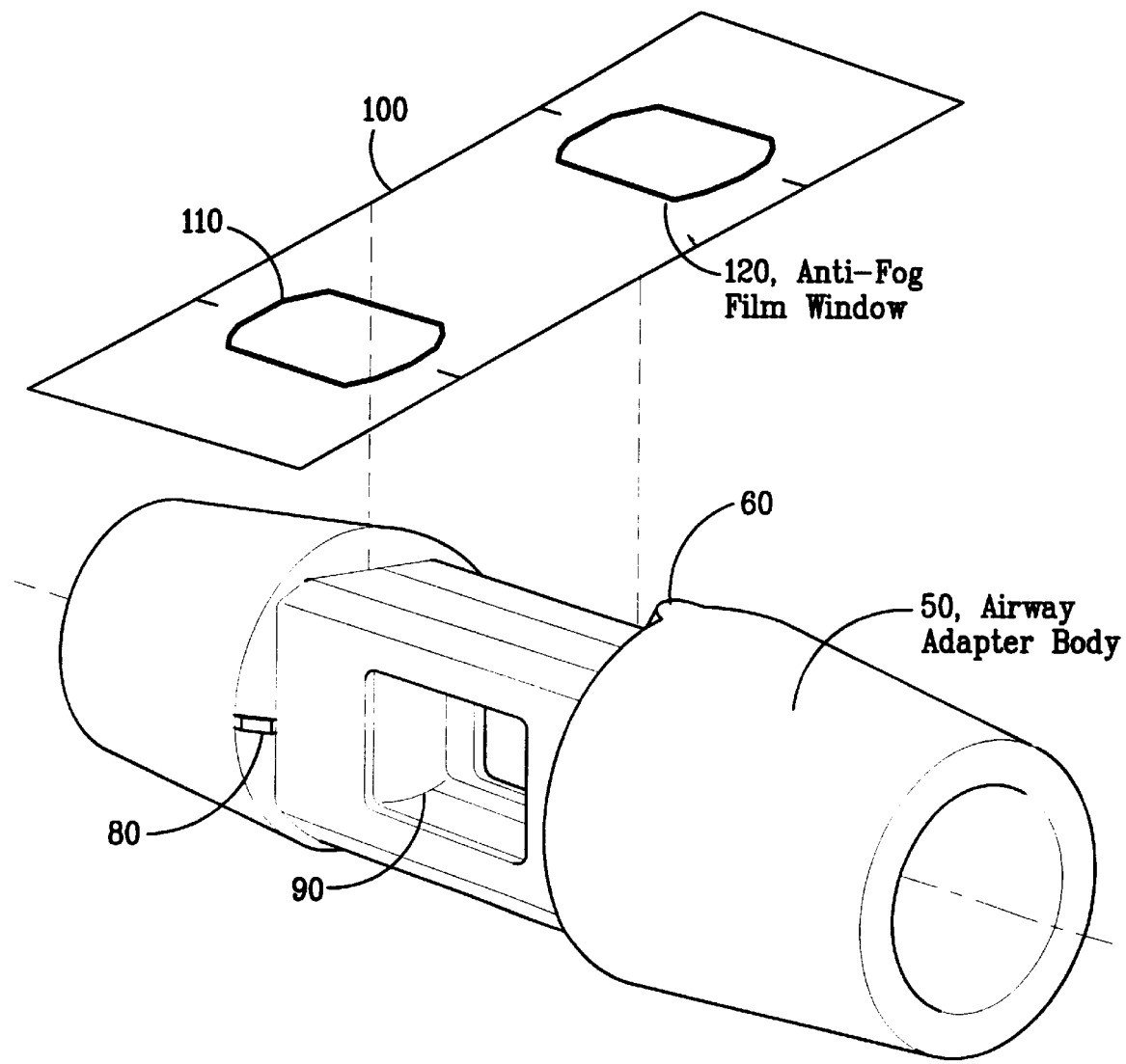

There are two general ways of applying the anti-fog treatment to the airway adapter in accordance with the invention. First, as illustrated in FIG. 3, the opening 90 of the airway adapter 50 may be covered with a clear polyester film 100 having a layer of an impregnated anti-fog coating on one side. A preferred embodiment of such a polyester film is the "Vistex 75" film available from Film Specialties, Inc., Whitehouse, N.J. Unlike other anti-fog treatments, the anti-fog coating of the "Vistex 75" film is permanent and does not wash out. As described in U.S. Pat. No. 4,467,073, such a coating is transparent. Preferably, the coating can be adhered to using a transfer adhesive such as Acrylic A-10 F9460 VHB available from 3M Corporation or its equivalent. On the other hand, a medically approved anti-fog treatment such as Atmer® (described above) may be used as the anti-fog coating. Atmer® may be applied after the windows have been installed into the airway adapter by pouring a solution of liquid Atmer® into the airway adapter body so as to cover the windows, draining the solution and then drying the windows in warm air as described above. This method provides very good anti-fog properties but has a limited service life since the Atmer® may wash off with use.

The above-mentioned method of providing a permanent anti-fog coating is presently preferred because of the long service life of the anti-fog coating and because there is no residue of dissolved anti-fog coating in the airway to deal with. Several methods of window installation to the airway adapter body will now be described with respect to FIGS. 3–7.

As illustrated in FIGS. 3(*a*) and 3(*b*), two anti-fog film windows may be applied to airway adapter body 50 by wrapping and sealing a thin infrared transmissive film 100 which is approximately 1 to 1.5 mils thick around the waist portion of the airway adapter body 50 over the openings 90. The thin film 100 applied to both sides of the airway adapter body 50 is disposed in the infrared transmission path and also functions as a part of the sealing mechanism for the airway adapter. FIG. 3(*b*) illustrates how the thin film 100 is wrapped about the airway adapter body 50 so that preprinted window outlines 110 align with the openings 90. The preprinted outlines 110 hide the edges of the openings 90 in the body 50 and also eliminate edge effects of the water's meniscus.

In a preferred embodiment, there are two processes of window application that are acceptable for adhering the thin film 100 to the airway adapter body 50 so as to provide a substantially air-tight seal of the film 100 over the opening 90. In a preferred embodiment, a pressure sensitive adhesive is disposed on the film 100 so as to provide a very simple and very reliable method of window application. The pressure sensitive adhesive such as Acrylic A-10 #F9460 from 3M Corporation is either selectively applied or die-cut to shape so that no adhesive is within the pre-printed window outline 110 of the thin window film 100. This method allows either anti-fog implementation as described above to be used. In other words, the film 100 may include an integral laminated anti-fog layer which is on the order of 0.5 mil of the 1 to 1.5 mil thick treated window, or the window 100 may be coated with a surfactant such as Atmer® 685 and the like after the windows have been formed.

FIG. 4(a) illustrates a 1.5 mil thick anti-fog film 100 having pre-printed window outlines 110 about window portions 120. Preferably, anti-fog film 100 is additionally printed with a black permanent ink to provide labeling information such as trademark information, patent labeling and the like. A transfer adhesive layer 130 is also provided with die-cut window portions 120. The transfer adhesive layer 130 is preferably 2 mils thick and is laminated to the anti-fog side of the film 100. Also, a release liner 140 is also preferably provided for the transfer adhesive layer 130 and is not removed until the film 100 is to be applied to the airway adapter body 50. The window label illustrated in FIG. 4(a) may be manually applied to the airway adapter body 50 by hand or by a machine.

FIG. 4(b) illustrates an alternative embodiment similar to that of FIG. 4(a) except that a copper layer 145 having window portions 120 is placed between the film 100 and the release liner 140 as illustrated. As shown, a further transfer adhesive layer 130 is provided to adhere the copper layer 145 to the film 100 and the release liner 140. Copper layer 145 functions to optimize heat distribution from the source of the infrared detection apparatus about the airway adapter body 50 so as to prevent further condensation from forming on the detector side of the airway adapter body 50 because of temperature differences from the source side of the airway adapter body 50 to the detector side of the airway adapter body 50. Copper layer 145 is wrapped about the airway adapter body 50 in the same manner as for the embodiment of FIG. 4 (a) so that window portions 120 align with the infrared detection apparatus.

On the other hand, the thin film 100 may be heat sealed to the airway adapter body 50 so as to provide a substantially air-tight seal. In such an embodiment, a reliable heat-bond seal using a film such as "Monokote®"is provided which has a layer of heat sensitive adhesive that requires a specific temperature and pressure for application to the airway adapter body 50. A special fixture is thus required to provide this type of window installation. However, heat sensitive adhesive in the window area may interfere with the anti-fog treatment. Accordingly, the aforementioned pressure sensitive adhesive is presently preferred.

Thus, the airway adapter window in accordance with a presently preferred embodiment of the invention can be fabricated like a label with a dye-cut transfer adhesive 130 which is pre-laminated. Alignment marks may also be printed on the label to facilitate visual or—optical alignment of the label with respect to the airway adapter body 50. In addition, the pre-printed window outlines 110 can be aligned to the corresponding airway adapter body openings 90 so that the window outline acts as mask to allow for a meniscus of condensed water to build up around the perimeters of the windows without affecting the optical path of the gas analyzer 40. The pre-printed window outlines 110 also may be used by the gas analyzer 40 as an aperture to detect if the airway adapter is misaligned or improperly installed in the airway adapter housing 30.

In the embodiment of FIGS. 3 and 4, the film 100 is wrapped around the circumference of the adapter body 50 and sealed as just described. The window pretension is achieved by maintaining tension on the film 100 as it is wrapped around the airway adapter body 50. The seal is accomplished by applying a pressure sensitive adhesive to the film 100 or the adapter body 50 before wrapping. Alternatively, a thermoset adhesive coating on the film 100 can be activated by a hot roller during wrapping. As illustrated in FIG. 3(b), the wrapping can begin and end on the sides of the body orthogonal to the optical path so that no seams or overlaps obstruct the optical path. The bond should then be tested to make sure that there is a continuous seal between the film 100 and the adapter body 50.

As noted above, the film 100 of the anti-fog airway adapter 90 need not be permanently treated but may be treated using a solution of a suitable non-toxic surfactant such as Atmer® 685. In such embodiments, the windows 120 are preferably formed of a polyester available from DuPont Corporation under the trade name "Mylar" and attached to the airway adapter body 50 in accordance with any of the techniques set forth herein by way of example. For example, a thin film of the type described above with respect to FIG. 3 may be formed which does not have an anti-fog coating laminated thereto, and this film may be wrapped around the airway adapter body 50 as previously described. The window portions 120 within the pre-printed window out-lines 110 of the film 100 may then be treated using a solution of a suitable non-toxic surfactant such as Atmer® 685 which is formed by mixing 7% ethanol, 5% Atmer® 685 and 88% water. Of course, stronger solutions may be mixed as desired. This solution is then poured into the completed airway adapter, drained and then dried in warm air (approximately 150° F.) for 15 minutes.

Figure 5:
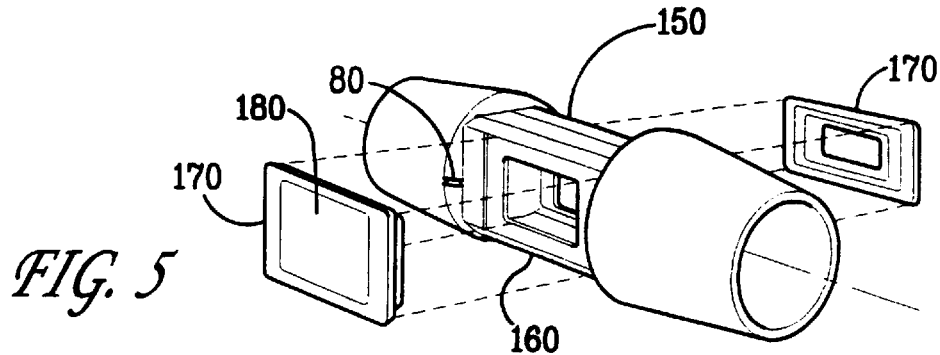
FIG. 5 illustrates a second embodiment of an anti-fog airway adapter of the invention whereby the windows are formed as window assemblies which are then sealed to the airway adapter prior to coating with a solution of a non-toxic surfactant.
Figure 6A:
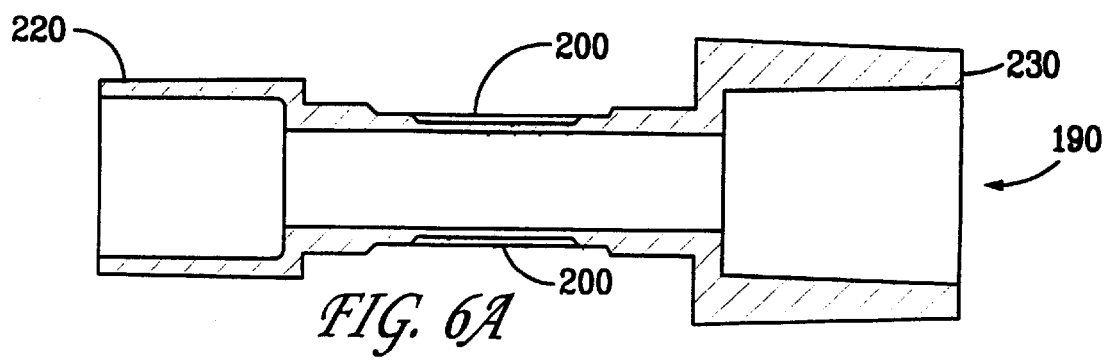
FIGS. 6(a)–(c) respectively illustrate top, interior side and exterior side views of an anti-fog airway adapter in accordance with a third embodiment of the invention.
Figure 6B:
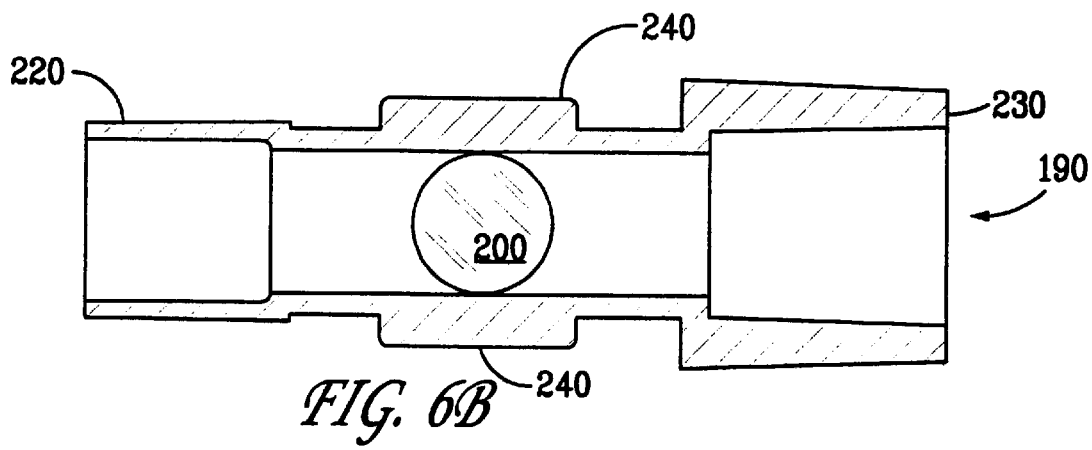
Figure 6C:
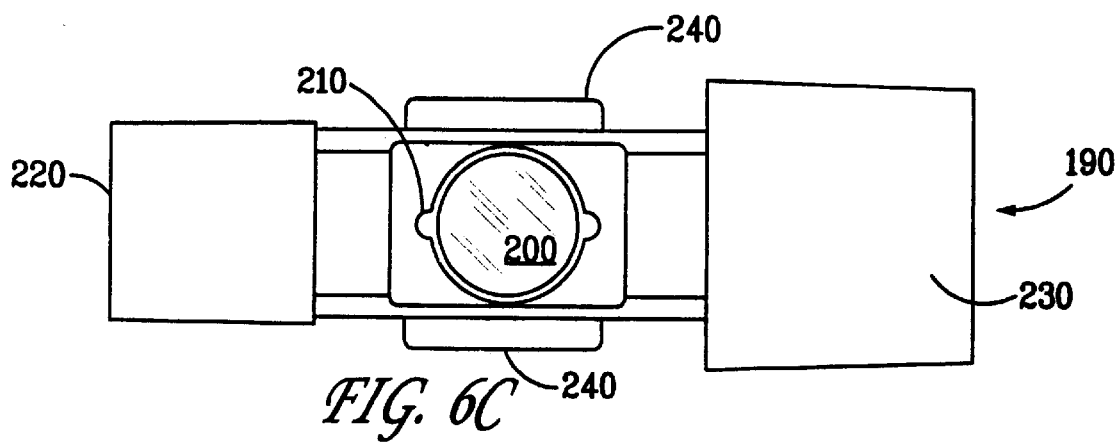

In an alternative embodiment illustrated in FIG. 5, the airway adapter body 150 instead may be molded so as to have openings 160 for mating with window assemblies 170 having windows 180. In such an embodiment, the film from which the windows 180 are formed is first treated with a thin layer of thermoset adhesive by means known to those skilled in the art. A sheet of such treated film, for example, about 10 inches square, is then stretched in a silk screening frame to a tension of about 10 psi. Then window frames, which are preferably molded out of the same material as the airway adapter body 150, are heat sealed to the stretched film to form the window assemblies 170. In a preferred embodiment, about 100 window frames can be sealed onto one stretched panel. The window frames can subsequently be cut from the panel and the film sealed in its prestressed condition. The window assembly 170 can then be sealed into a mating feature in the opening 160 of the airway adapter body 150 by solvent bonding, ultrasonic welding, or both, or some other technique so long as a substantially airtight seal may be obtained. A clear, free flowing solvent such as methylene chloride may be used to bond the adapter frame assembly 170 to the airway adapter body 150 so long as the bonded joint is complete and clear with no overflow marks, stains and the like.

FIGS. 6(a)–6(c) and 7 illustrate a third technique for forming the windows of the airway adapter 190. In this embodiment, the thin layer 195 which forms the optical windows 200 is preferably placed on a drum head 205 and then adhered to the adapter body 190 over the opening for the windows 200 and held in place by a drum band 210 which is preferably molded out of plastic which can stretch to the desired tension or is formed from rubber into a rubber band. In other words, the manufacturing process comprises the steps of molding the airway adapter body 190, cutting a drum band 210 which fits over a drum head 205 and layer 195 as shown in FIG. 7, and adhering the drum head assembly to the airway adapter body 190 by heat pressing the periphery of the window 200 about the drum band using a heat staking technique, by snap-fitting the drum band about the drum head, or by adhering the window 200 to the adapter body 190 by some other acceptable adhering technique. As described above, the airway adapter body 190 is preferably formed by injection molding while the adhering is preferably done through ultrasonic bonding, inertial welding or by using a suitable adhesive. In addition, to ensure sufficient optical quality using this technique, the windows 200 are preferably formed to be 0.001±0.0005 inch thick. This thickness represents an acceptable trade-off between mechanical integrity and light absorption capabilities. As a result, the airway adapter of the invention may be manufactured very inexpensively while remaining structurally strong. Finally, so that the airway adapter may fit snugly into the respiratory airstream of the patient, tapered ends 220 and 230 as well as snap-fitting tabs 240 are provided as described in U.S. Pat. No. 5,067,492.

In accordance with a fourth technique for forming the windows of the airway adapter of the invention, the manufacturing process for the airway adapter is modified such that following the initial molding of the airway adapter body a "hot stamping" operation is performed which details the optical window sections by squeezing them thinner and flatter between two heated surfaces that are polished to optical quality. The hot stamped window may then be polished to optical quality as desired. The result is a clear, thin optical window which is inherently part of the airway adapter body. Since the resulting airway adapter is formed of only a single piece, it is structurally stronger and substantially less expensive than some of the other embodiments.

In accordance with a fifth technique for forming the windows of the airway adapter of the invention, the window film is extruded into a tube by means known to those skilled in the art such that the inside circumference of the tube is approximately 5% greater than the outside circumference of the airway adapter body. The tube is then cut to length and threaded over the airway adapter body to its proper location. The tube is subsequently shrunken by the application of heat from a hot air gun or an oven so that a tight fit around the body circumference is achieved for the necessary airtight seal. The necessary window prestress is accomplished in this heat shrinking step. In addition, if additional gas sealing is desired, the inside surface of the tube may be treated with a thermoset or UV curing adhesive. The thermoset adhesive should have an activation temperature of about 10° C. higher than the shrink temperature of the polyester film, which is about 85° C. in a preferred embodiment. After shrinking, the thermoset adhesive can be activated by it hot stamp which provides additional sealing.

The optical transmission characteristics of the materials used for the windows in the present invention (preferably, polyester, polyethylene or polypropylene) are not flat within the region of interest. Since each window is not spectrally flat, "differential absorption" effects may adversely affect the resulting analyzer reading. Accordingly, to accommodate this "differential absorption" the gas analyzer 40 in accordance with the present invention is calibrated at the completion of the manufacturing process with a representative sample with the windows in place. When thus calibrated, the effect of the component materials of the windows is taken into account so that the gas analyzer 40 is able to operate accurately with the airway adapter 10 in place for normal use. Since this calibration is done at the factory, it is of no burden to the user.

Figure 8:
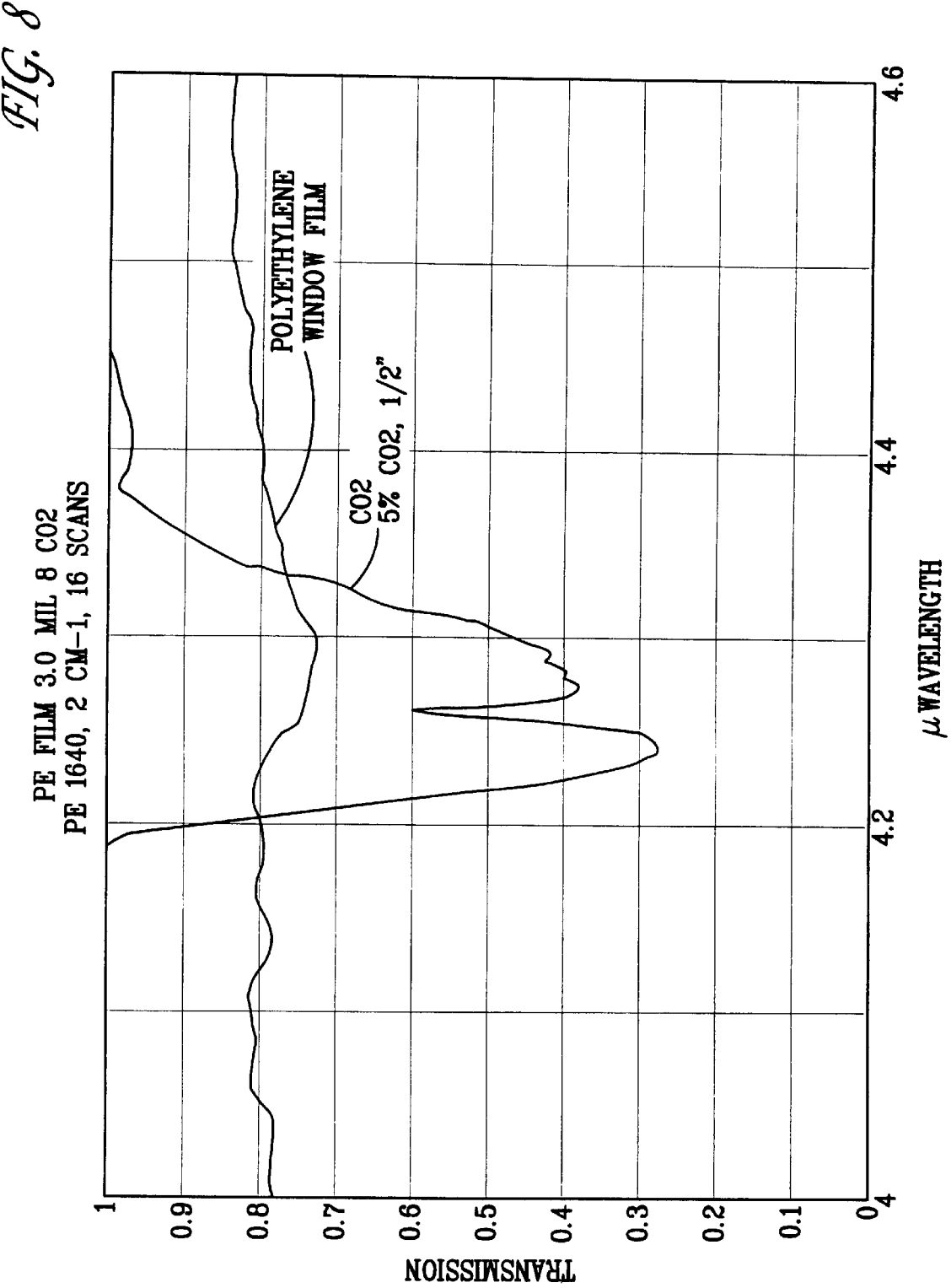
FIG. 8 illustrates an absorption spectrum in the region of interest for polyethylene and $CO_2$ gas.

FIG. 8 illustrates the absorption spectrum in the region of interest for polyethylene and $CO_2$ gas. As just described, FIG. 8 illustrates that the spectrum for polyethylene used in the windows is not spectrally "flat" and thus must be accommodated in the calibration of the gas analyzer 40 for accurate readings to result. This calibration is necessary in accordance with the invention, for in the production of disposable airway adapters it is critical that each window have the same infrared absorption spectrum in the region of interest so that all windows are functionally interchangeable. The airway adapter of the present invention is thus preferably used with a gas analyzer 40 which has been designed so as to relax the optical requirements on the windows. Such an optical analyzer is disclosed, for example, in the aforementioned related parents assigned to the present assignee. Thus, each window manufactured must have identical absorption spectra in the wavelengths of interest, which is controlled by the chemical composition of the material used to form the window. Accordingly, during manufacture, the windows are constrained in the apertures of the airway adapter body during bonding so as remain flat. Anti-reflection coatings may be placed on the thin films so as to avoid reflection of the infrared light.

Although numerous exemplary embodiments of the invention have been described in detail above, those skilled in the art will readily appreciate that many additional modifications are possible in the exemplary embodiments without materially departing from the novel teachings and advantages of the invention. For example, to further decrease the adverse effects of water droplets on the infrared measurement, the inside portion of the airway adapter body 50 adjacent the window preferably is designed to include "gutters" for channeling condensed water droplets away from the sill formed at the window openings. Accordingly, all such modifications are intended to be included within the scope of this invention as defined in the following claims.

We claim:

1. An endotracheal airway adapter for use in a respiratory airstream of a patient in proximity of the patient's mouth during quantitative measurement of the concentration of respiratory constituents of the patient using a respiratory analyzer having infrared transmission and detection devices disposed in a housing which receives said airway adapter, said airway adapter comprising:

a substantially tubular portion comprised of a material which is slightly deformable and has oppositely disposed openings in a width-wise direction thereof which lie in an optical path between said infrared transmission and detection devices when received by said housing;

a pair of thin plastic windows respectively disposed over said oppositely disposed openings of said tubular portion so as to form a substantially airtight seal and so as to be a predetermined distance from each other during said quantitative measurement of the concentration of respiratory constituents of the patient using said infrared transmission and detection devices, said windows passing infrared energy from said infrared transmission device to said detection device; and a non-toxic anti-fog surfactant which treats said windows so as to prevent fogging of said windows when said windows are placed in the respiratory airstream of the patient.

2. The airway adapter of claim 1, wherein said tubular portion is formed from a material including at least one of a polycarbonate, styrene acrylonitrate and aluminum.

3. The airway adapter of claim 2, wherein said windows are formed from a material including at least one of polyester, polypropylene and polyethylene.

4. The airway adapter of claim 1, wherein said windows comprise a single thin plastic layer including said anti-fog surfactant impregnated therein so as to form an anti-fog film approximately 1 to 1.5 mil thick.

5. The airway adapter of claim 4, further comprising a thin copper layer disposed between said anti-fog film and said tubular portion so as to distribute heat from said infrared transmission device over the surface of said tubular portion.

6. The airway adapter of claim 4, further comprising a heat seal adhesive which forms said substantially airtight seal between said anti-fog film and said tubular portion.

7. The airway adapter of claim 4, further comprising a pressure sensitive adhesive which forms said substantially airtight seal between said anti-fog film and said tubular portion.

8. The airway adapter of claim 1, wherein said anti-fog surfactant comprises a solution which forms a layer over said windows when poured into said airway adapter over said windows, said solution is drained, and then said windows are dried in warm air.

9. The airway adapter of claim 8, further comprising a heat seal adhesive which forms said substantially airtight seal between said thin plastic windows and said tubular portion.

10. The airway adapter of claim 8, further comprising a pressure sensitive adhesive which forms said substantially airtight seal between said thin plastic windows and said tubular portion.

11. The airway adapter of claim 1, wherein each of said thin plastic windows comprises a stretched sheet of polymer film.

12. The airway adapter of claim 11, wherein said adapter further comprises a pair of frames to which said stretched sheets are heat sealed to form respective window frame assemblies for placement in said oppositely disposed openings.

13. The airway adapter of claim 12, further comprising a drum band disposed over said window frame assemblies about the periphery of said oppositely disposed openings so as to hold said window frame assemblies in place in said oppositely disposed openings.

14. The airway adapter of claim 1, further comprising a thin plastic layer containing said pair of thin plastic windows disposed such that when said thin plastic layer is wrapped around said tubular portion said respective thin plastic windows are disposed over said respective oppositely disposed openings.

15. The airway adapter of claim 1, wherein said pair of thin plastic windows comprise a heat shrink tube shrunk about said tubular portion so as to cover said respective oppositely disposed openings.

16. An endotracheal airway adapter for use in a respiratory airstream of a patient in proximity of the patient's mouth during quantitative measurement of the concentration of respiratory constituents of the patient using a respiratory analyzer having infrared transmission and detection devices disposed in a housing which receives said airway adapter, said airway adapter comprising:

a substantially tubular portion comprised of a material which is slightly deformable and has oppositely disposed openings in a width-wise direction thereof which lie in an optical path between said infrared transmission and detection devices when received by said housing;

an anti-fog film including a thin plastic layer impregnated with a non-toxic anti-fog surfactant, said anti-fog film containing a pair of thin plastic windows formed therein and disposed such that when said anti-fog film is wrapped around said tubular portion said respective thin plastic windows are disposed over said respective oppositely disposed openings of said tubular portion so as to form a substantially airtight seal and so as to be a predetermined distance from each other during said quantitative measurement of the concentration of respiratory constituents of the patient using said infrared transmission and detection devices, said windows passing infrared energy from said infrared transmission device to said detection device; and a thin copper layer disposed between said anti-fog film and said tubular portion so as to distribute heat from said infrared transmission device over the surface of said tubular portion.

17. A method of forming an endotracheal airway adapter having anti-fog windows for use in a respiratory airstream of a patient in proximity of the patient's mouth during quantitative measurement of the concentration of respiratory constituents of the patient using a respiratory analyzer having infrared transmission and detection devices disposed in a housing which receives said airway adapter, comprising the steps of:

respectively disposing a pair of thin plastic windows over oppositely disposed openings of a substantially tubular portion comprised of a material which is slightly deformable and has said oppositely disposed openings in a width-wise direction thereof which lie in an optical path between said infrared transmission and detection devices when received by said housing, said pair of thin plastic windows and said oppositely disposed openings forming a substantially airtight seal and said pair of thing plastic windows being a predetermined distance from each other during said quantitative measurement of the concentration of respiratory constituents of the patient using said infrared transmission and detection devices, said windows passing infrared energy from said infrared transmission device to said detection device; and treating said windows with a non-toxic anti-fog surfactant so as to prevent fogging of said windows when said windows are placed in the respiratory airstream of the patient.

18. The method of claim 17, wherein said treating step comprises the step of impregnating a single thin plastic layer with said anti-fog surfactant so as to form an anti-fog film approximately 1 to 1.5 mil thick.

19. The method of claim 18, comprising the additional step of disposing a thin copper layer between said anti-fog film and said tubular portion so as to distribute heat from said infrared transmission device over the surface of said tubular portion.

20. The method of claim 17, wherein said treating step comprises the steps of pouring a solution of said anti-fog surfactant over said windows so as to form a layer over said windows, draining said solution, and drying said windows in warm air.

21. The method of claim 17, wherein said disposing step comprises the steps of stretching a sheet of polymer film over said oppositely disposed opening and heat sealing said stretched sheet to a pair of frames to form respective window frame assemblies and placing said window frame assemblies in said oppositely disposed openings.

22. The method of claim 21, wherein said disposing step further comprises the step of disposing a drum band over said window frame assemblies about the periphery of said oppositely disposed openings so as to hold said window frame assemblies in place in said oppositely disposed openings.

23. The airway adapter of claim 17, wherein said disposing step comprises the step of heat shrinking a tube about said tubular portion so as to cover said respective oppositely disposed openings.

* * * * *